US00PP15259P2

(12) United States Plant Patent
Bradford

(10) Patent No.: US PP15,259 P2
(45) Date of Patent: Oct. 19, 2004

(54) PEACH TREE NAMED "SUGARPEACH"

(50) Latin Name: *Prunus persica*
Varietal Denomination: Sugarpeach

(76) Inventor: Lowell Glen Bradford, 12439 E. Savana Rd., Le Grand, CA (US) 95333

( * ) Notice: Subject to any disclaimer, the term of this patent is extended or adjusted under 35 U.S.C. 154(b) by 0 days.

(21) Appl. No.: 10/746,770

(22) Filed: Dec. 29, 2003

(51) Int. Cl.[7] ..... A01H 5/00
(52) U.S. Cl. ..... Plt./197
(58) Field of Search ..... Plt./197

(56) References Cited

U.S. PATENT DOCUMENTS

PP6,363 P 11/1988 Bradford

PP7,066 P 12/1989 Bradford

*Primary Examiner*—Kent Bell

*Assistant Examiner*—S. B. McCormick-Ewoldt

(57) ABSTRACT

The present invention relates to a peach tree, *Prunus persica,* and more particularly to a new and distinct variety characterized by a medium size, vigorous, hardy, self-fertile, productive and regular bearing tree. The fruit matures under the ecological conditions described in mid July, with first picking on Jul. 16, 2003. The fruit is very large in size, sweet and acidic in flavor, globose with some tipping on the apex in shape, clingstone in type, yellow with significant red bleeding in flesh color, mostly red in skin color, and extremely firm to non-melting in texture. The present variety was the result of a nectarine by peach hybridization.

1 Drawing Sheet

Botanical classification: *Prunus persica.*
Variety denomination: 'Sugarpeach'.

BACKGROUND OF THE VARIETY

In a continuing effort to improve the quality of shipping fruits, I, the inventor, typically hybridize a large number of peach, nectarine, plum, apricot, and cherry seedlings each year. The present invention relates to a new and distinct variety of peach tree, which has been denominated varietally as 'Sugarpeach'. The present variety was hybridized by me in 1988, grown as a seedling on its own root in my greenhouse, and transplanted to a cultivated area of my experimental orchard at Bradford Farms near Le Grand, Calif. in Merced County (San Joaquin Valley). The variety was developed as a first generation cross using 'August Red' (U.S. Plant Pat. No. 6,363) nectarine as the selected seed parent and 'Diamond Princess' (U.S. Plant Pat. No. 7,066) peach as the selected pollen parent. Subsequent to origination of the present variety of peach tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to its selected seed parent, 'August Red' (U.S. Plant Pat. No. 6,363) nectarine, by producing fruit that is firm and crisp in texture, mostly red in skin color, yellow in flesh color, and clingstone in type, but is very distinguished therefrom by producing fruit that is peach instead of nectarine and that ripens about forty days earlier.

The present variety is similar to its selected pollen parent, Diamond Princess (U.S. Plant Pat. No. 7,066) peach, by producing peaches that are nearly full red in skin color, sweet and acidic in flavor, and globose in shape, but is distinguished therefrom by having a small blossom instead of large and by producing fruit that is clingstone instead of freestone, that is firmer and virtually non-melting in flesh texture, that is yellow with dark red bleeding in the flesh color, that holds on the tree much longer, that has a protruding tip at the apex on many, that is much larger in size, and that matures about ten days later.

SUMMARY OF VARIETY

In summary, the present variety is characterized by a medium size, vigorous, hardy, self-fertile, productive and regular bearing tree. The fruit matures under the ecological conditions described in mid July, with first picking on Jul. 16, 2003. The fruit is very large in size, sweet and acidic in flavor, globose with some tipping on the apex in shape, clingstone in type, yellow with significant red bleeding in flesh color, mostly red in skin color, and extremely firm to non-melting in texture. The present variety was the result of a nectarine by peach hybridization.

DRAWING

The accompanying photograph exhibits four whole fruits positioned to display the characteristics of the skin color and form, one fruit divided transversely to the suture plane to reveal the flesh and stone, and typical leaves.

POMOLOGICAL CHARACTERISTICS

Referring now more specifically to the pomological characteristics of this new and distinct variety of peach tree, the following has been observed under the ecological conditions prevailing near Le Grand, Merced County (San Joaquin Valley), Calif., and was developed at the state of firm ripe on Jul. 20, 2003, on the original tree during its fifteenth growing season. All major color code designations are by reference to the Inter-Society Color Council, National Bureau of Standards. Common color names are also used occasionally.

Tree

Size: Medium, reaching a height of 12' [3.7 m.] and a spread of 10' [3.0 m.] after fifteen growing seasons utilizing typical dormant pruning.

Vigor: Vigorous, responding typically to irrigation and fertilization. The variety grows about 3' [0.9 m.] of surplus top-growth during the spring and summer. The plant should be grown on a standard commercial rootstock for production purposes.

Growth: Spreading and dense.

Form: Trained to a two leader V-shape by pruning.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive, thinning necessary.

Fertility: Self-fertile.

Bearing: Regular bearer with no alternate bearing yet observed.

Trunk:

*Size.*—Medium, with a maximum diameter of 6.5" [165 mm.] after the fifteenth growing season.

*Texture.*—Shaggy.

*Bark color.*—Dark grayish reddish brown [47. d.gy.rBr].

*Lenticels.*—Approximate number per square inch: 10. Color: Moderate orange yellow [71. m.OY]. Average size: ⅛" to ½" [3.2–12.7 mm.].

Branches:

*Size.*—Diameter of limb is 3¾" [95 mm.] measures 12" above the crotch and 2½" [64 mm.] measured 12" above the secondary fork, typical of *Prunus persica,* and dependent upon cultural practices and climatic conditions.

*Texture.*—Smooth on 1st year wood, increasing roughness with age.

*Color.*—1st year wood topside: Light grayish red [18. l.gy.R]. 1st year wood underside: Brilliant yellow green [116. brill.YG]. Older wood: Deep yellowish brown [75. deep yBr].

*Lenticels.*—Approximate number per square inch: 100. Color: Moderate orange yellow [71. m.OY]. Typical size: 1/32" to ⅛" [0.8–3.2 mm.].

Leaves:

*Size.*—Large. Average length: 1¾" [45 mm.]. Average width: 6¾" [159 mm.].

*Arrangement.*—Alternate.

*Thickness.*—Medium.

*Form.*—Elliptical.

*Apex.*—Acuminate.

*Base.*—Acute with an average base angle of 80 degrees.

*Surface.*—Smooth.

*Color.*—Dorsal surface: Moderate olive green [125 m.OlG]. Ventral surface: Moderate yellow green [120. m.YG].

*Margin.*—Finely serrate.

*Venation.*—Pinnately net veined.

*Petiole.*—Average length: ½" [12.7 mm.]. Average thickness: 1/16" [1.6 mm.]. Color: Moderate yellow green [120. m.YG].

*Stipules.*—Number: Up to 2 per leaf and 6 per growing tip. Average length: ¼" [6.4 mm.]. Color: Brilliant yellow green [116. brill.YG] becoming Dark grayish reddish brown [47. d.gy.rBr] with age.

*Glands.*—Number: 2 to 4. Position: The first two are alternately or oppositely positioned on the petiole with the remainder usually on the basis of leaf blade. Size: Medium. Form: Reniform. Color: Brilliant yellow green [116. brill.YG] on the outside edges with Grayish reddish brown [46. gy.rBr] centers.

*Leaf buds.*—Medium, pointed.

Flower buds:

*Hardiness.*—Hardy, with respect to central California winters.

*Diameter.*—Typically 5/16" [7.9 mm.] 1 week before bloom.

*Length.*—Typically ½" [12.7 mm.] 1 week before bloom.

*Form.*—Not appressed.

*Surface.*—Pubescent.

*Color.*—Strong purplish pink [247. s.pPk].

Flowers: Perfect, complete, perigynous, usually a single pistil, typically thirty or more stamens, five sepals and petal locations alternately positioned.

*Type.*—Non-showy, small.

*Average flower diameter.*—15/16" [23.8 mm.].

*Number of petals.*—Usually five.

*Petal shape.*—Oval.

*Petal margin.*—Somewhat wavy.

*Average petal diameter.*—7/16" [11.1 mm.].

*Average petal length.*—9/16" [14.3 mm.].

*Petal apex.*—Rounded.

*Petal base.*—Acute.

*Petal color.*—Pale purplish pink [252. p.pPk] toward the apex smoothly blending to strong purplish pink [247. s.pPk] toward the base.

*Anther color.*—Deep reddish orange [36. deep rO] over a Brilliant orange yellow [67. brill.OY] center.

*Stigma color.*—Light greenish yellow [101. l.gY].

*Sepal color.*—Dark purplish red [259. d.pR].

*Sepal length.*—¼" [6.4 mm.].

*Sepal width.*—3/16" [4.8 mm.].

*Average pistil length.*—11/16" [17.5 mm.].

*Average stamen length.*—½" [12.7 mm.].

*Fragrance.*—Moderate when nectar is present.

*Blooming period.*—About five days later than average compared with other varieties.

*Onset of bloom.*—One percent on Mar. 7, 2003.

*Date of full bloom.*—Mar. 15, 2003.

*Duration of bloom.*—One to two weeks, dependent on ambient temperature.

*Number per cluster.*—1 to 3 with single flowers most common.

Fruit

Maturity when described: Firm ripe, Jul. 20, 2003.

Date of first picking: Jul. 16, 2003.

Date of last picking: Jul. 30, 2003.

Size: Uniform, very large.

*Average diameter axially.*—3 5/16" [84 mm.].

*Average diameter across suture plane.*—3⅜" [86 mm.].

*Typical weight.*—11.5 ounces [326 grams].

Form: Uniform, globose, some slightly asymmetrical.
*Longitudinal section form.*—Circular to oval.
*Transverse section through diameter.*—Circular.
Suture: A distinct line located in a groove near the base, a shallow groove along the sides, and a deeper groove toward the apex discontinuing with a marked depression just beyond the pistil point.
Ventral surface: Rounded, lipped slightly.
Lips: Somewhat unequal.
Gravity: Flaring, elongated in the suture plane, suture showing on one side, Light yellow [86. l.Y] stem markings typical.
*Depth.*—¾" [19.1 mm.].
*Breadth.*—1⅛" [28.6 mm.].
Base: Rounded to truncate.
Apex: Rounded and usually mammiform.
Pistil point: Both apical and oblique, located at the end of a mammiform tip of length ¼" [6.4 mm.].
Stem: Medium.
*Average length.*—7/16" [11.1 mm.].
*Average width.*—3/16" [4.8 mm.].
Skin:
*Thickness.*—Medium, tough.
*Surface.*—Pubescent.
*Tenacity.*—Tenacious to flesh.
*Astringency.*—Slightly astringent.
*Tendency to crack.*—None observed.
*Color.*—Very deep red [14. v.deep R] smoothly blending into a Strong reddish orange [35. s.rO] background with Brilliant yellow [83. brill.Y] areas where sun protected.
Down: Moderate, short in length, does not roll up when rubbed.
Flesh:
*Color.*—Brilliant Yellow [83. brill.Y] with an abundance of Dark red [16. d.R] streaking, bleeding and flecking throughout.
*Surface of pit cavity.*—Covered with strong orange [50. s.O] to Brilliant yellow [83. brill.Y] broken fibers when twisted away from the stone.
*Amygdalin.*—Moderate.
*Juice.*—Abundant, rich.
*Texture.*—Firm, crisp and non-melting.
*Fibers.*—Abundant, tough.
*Ripens.*—Slightly earlier at the apex.
*Flavor.*—A tasty blend of acid and sugar averaging 13 brix.
*Aroma.*—Moderate.
*Eating quality.*—Very good.

Stone

Type: Clingstone.
Form: Oval.
Hilum: Narrow, oblong.
Base: Straight.
Apex: Acute, with an average tip length of ⅛" [3.2 mm.] and an average tip angle of 70 degrees.
Sides: Equal.
Surface: Irregularly furrowed and ridged near the apex and pitted toward the base.
Ridges: Jagged toward the base.
External color: Deep yellowish brown [75. deep yBr].
Internal color when cracked: Moderate yellowish brown [77. m.yBr].
Cavity surface color: Strong yellowish brown [74. s.yBr].
Average pit wall thickness: ¼" [6.4 mm.].
Average width: 1⅛" [28.6 mm.].
Average length: 1⅝" [41.3 mm.].
Average breadth: 13/16" [20.6 mm.].
Tendency to split: Slight.
Kernel:
*Form.*—Oval.
*Pellicle color.*—Dark grayish yellow [91. d.gy.Y].
*Skin color.*—Pale yellow [89. p.Y] when freshly removed.
*Vein color.*—Grayish yellow [90. gy.Y].
*Taste.*—Bitter.
*Viable.*—Yes.
*Average width.*—½" [12.7 mm.].
*Average length.*—⅞" [22.2 mm.].
*Amygdalin.*—Abundant.

Use

Market: Fresh market and long distance shipping.
Keeping quality: Good. Fruit quality observed to remain in good condition after 17 days in standard cold room at 36° Fahrenheit [2° Celsius].
Shipping quality: Good.
Resistance to insects: No unusual susceptibilities noted.
Resistance to diseases: No unusual susceptibilities noted.

Other Notes

Although the new variety of peach tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of peach tree, substantially as illustrated and described, that is most similar to its selected pollen parent, 'Diamond Princess' (U.S. Plant Pat. No. 7,066) peach, by producing peaches that are mostly red in skin color, sweet and acidic in flavor, and globose in shape, but is distinguished therefrom by having a small blossom instead of large and by producing fruit that is clingstone instead of freestone, that is much firmer and virtually non-melting in flesh texture, that is yellow with dark red bleeding in flesh color, that holds on the tree much longer, that is much larger in size, and that matures about ten days later, all of which can be attributed to the selected seed parent 'August Red' (U.S. Plant Pat. No. 6,363) nectarine, and is further distinguished from both by having protruding tips at the apex on much of the fruit.

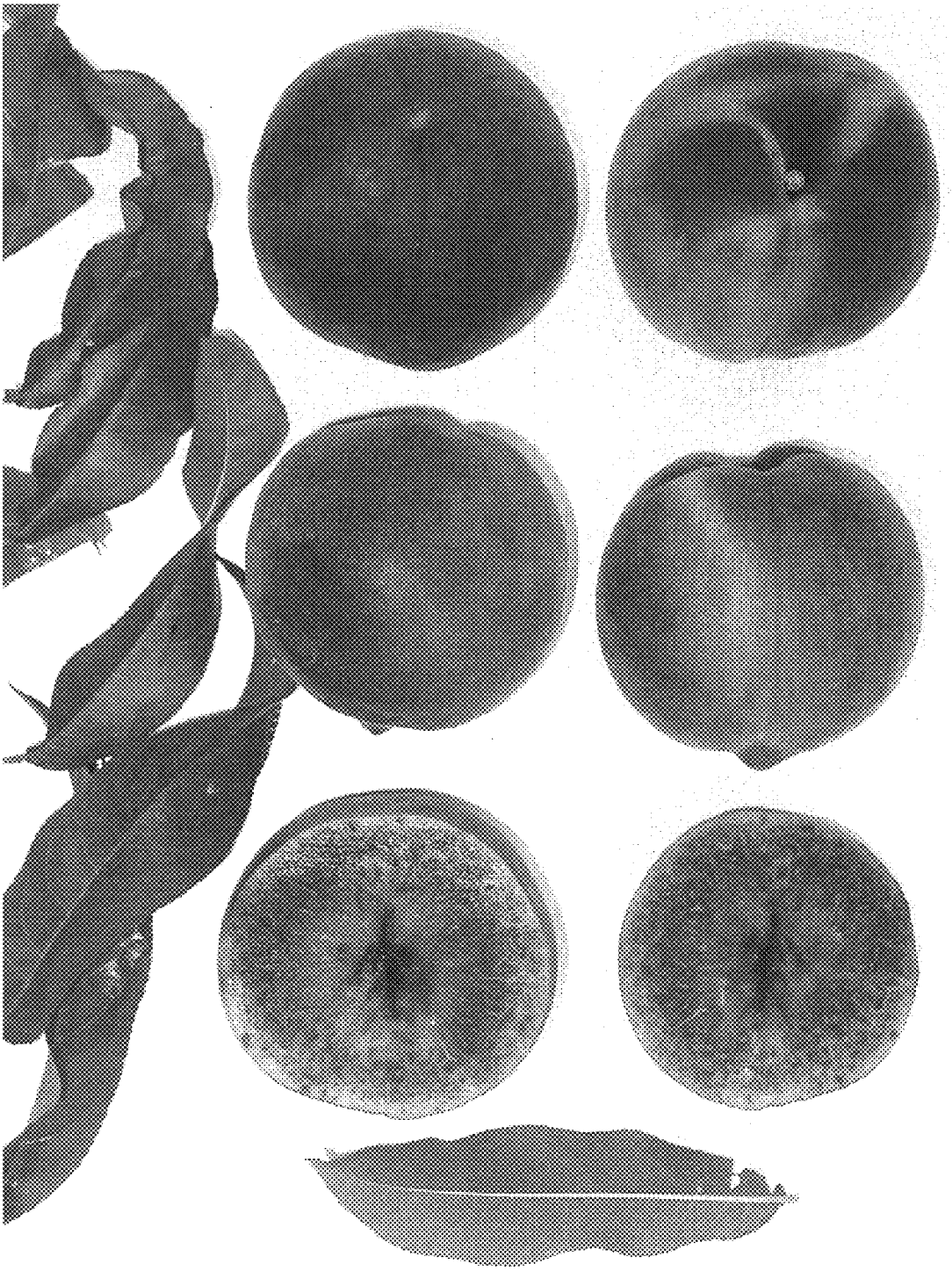

* * * * *